(12) United States Patent
Marcu et al.

(10) Patent No.: US 10,422,749 B2
(45) Date of Patent: Sep. 24, 2019

(54) FACILITATING REAL-TIME VISUALIZATION OF TISSUE FEATURES DERIVED FROM OPTICAL SIGNALS

(71) Applicant: The Regents of the University of California, Oakland, CA (US)

(72) Inventors: Laura Marcu, Davis, CA (US); Dinglong Ma, Davis, CA (US); Julien Bec, Davis, CA (US); Dimitris Gorpas, Davis, CA (US); Diego R. Yankelevich, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/538,081

(22) PCT Filed: Jan. 22, 2016

(86) PCT No.: PCT/US2016/014625
§ 371 (c)(1),
(2) Date: Jun. 20, 2017

(87) PCT Pub. No.: WO2016/118925
PCT Pub. Date: Jul. 28, 2016

(65) Prior Publication Data
US 2017/0370843 A1 Dec. 28, 2017

Related U.S. Application Data

(60) Provisional application No. 62/107,304, filed on Jan. 23, 2015, provisional application No. 62/281,329, filed on Jan. 21, 2016.

(51) Int. Cl.
*G01N 21/00* (2006.01)
*G01N 21/64* (2006.01)
*A61B 5/00* (2006.01)

(52) U.S. Cl.
CPC ....... *G01N 21/6456* (2013.01); *A61B 5/0071* (2013.01); *A61B 5/0077* (2013.01);
(Continued)

(58) Field of Classification Search
CPC .......... G01N 21/6428; G01N 21/6458; G01N 21/64; G01N 21/6408; G01N 2021/6421
See application file for complete search history.

(56) References Cited

U.S. PATENT DOCUMENTS

2002/0072677 A1* 6/2002 Sevick-Muraca .... A61B 5/0059
600/473
2005/0059894 A1 3/2005 Zeng et al.
(Continued)

OTHER PUBLICATIONS

International Search Report, PCT/US2016/014625, prepared by Blaine R. Copenheaver, dated Apr. 6, 2016.

*Primary Examiner* — David P Porta
*Assistant Examiner* — Mamadou Faye
(74) *Attorney, Agent, or Firm* — Park, Vaughan, Fleming & Dowler LLP

(57) ABSTRACT

The disclosed embodiments relate to a system that displays an image of the characteristics of the biological tissue. During operation, the system enables a user to illuminate a measurement location in an area of interest on the biological tissue by manipulating a point measurement probe, wherein the point measurement probe delivers both an excitation beam and an overlapping aiming beam that is visible to a camera. Next, the system obtains fluorescence information from a fluorescence signal emitted from the measurement location in response to the excitation beam. The system then captures an image of the area of interest using the camera and identifies a portion of the image that corresponds to the measurement location by identifying a location illuminated by the aiming beam. Finally, the system generates an overlay image by overlaying the fluorescence information onto the (Continued)

portion of the image that corresponds to the measurement location, and then displays the overlay image to a user.

28 Claims, 8 Drawing Sheets

(52) U.S. Cl.
CPC ....... *A61B 5/7425* (2013.01); *G01N 21/6486* (2013.01); *G01N 2021/6417* (2013.01)

(56) References Cited

U.S. PATENT DOCUMENTS

| | | | |
|---|---|---|---|
| 2009/0326384 A1* | 12/2009 | Bigio | A61B 5/0075 600/476 |
| 2010/0049055 A1* | 2/2010 | Freudenberg | A61B 5/0059 600/475 |
| 2010/0286529 A1* | 11/2010 | Carroll | A61B 1/0005 600/476 |
| 2012/0002012 A1* | 1/2012 | O'Grady | A61B 6/022 348/45 |
| 2012/0326055 A1* | 12/2012 | Wilson | A61B 5/0059 250/459.1 |
| 2014/0276008 A1* | 9/2014 | Steinbach | A61B 5/0071 600/424 |
| 2015/0182118 A1* | 7/2015 | Bradbury | A61B 1/043 600/431 |
| 2015/0362669 A1* | 12/2015 | Aizenberg | G01L 1/247 385/13 |

* cited by examiner

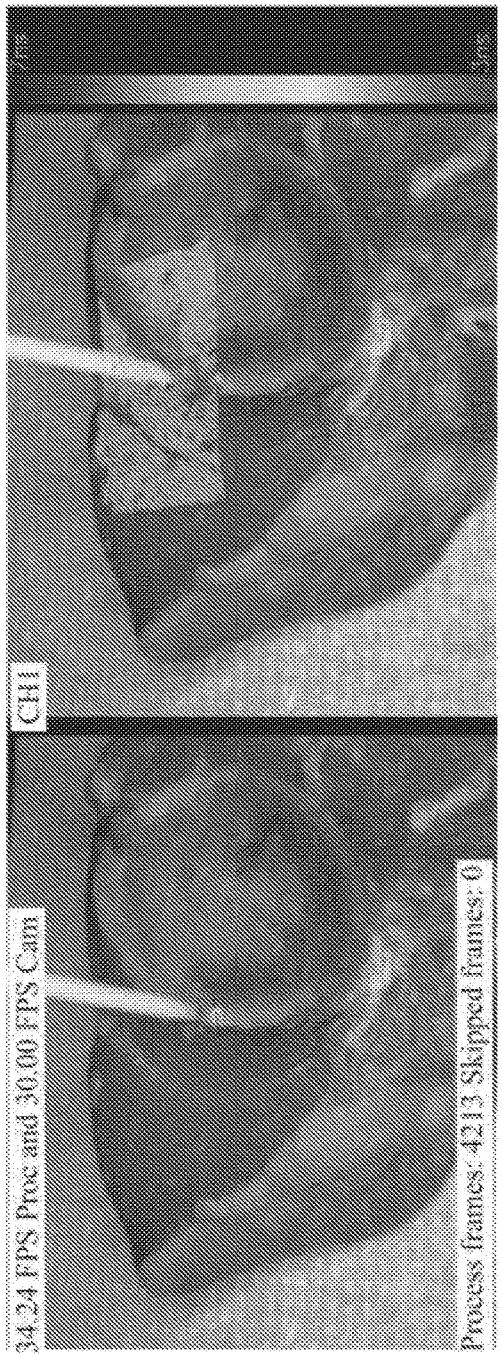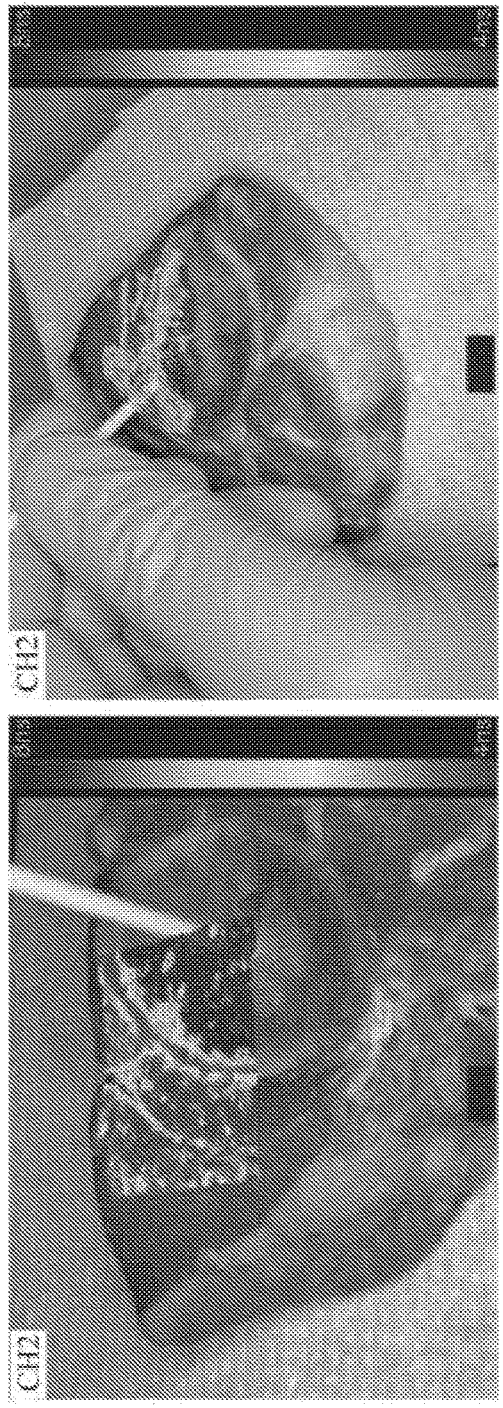
FIG. 6A
FIG. 6B
FIG. 6C

FACILITATING REAL-TIME VISUALIZATION OF TISSUE FEATURES DERIVED FROM OPTICAL SIGNALS

BACKGROUND

Field

The disclosed embodiments generally relate to methods for using fluorescence imaging techniques to analyze biological tissues. More specifically, the disclosed embodiments relate to the design of a system that facilitates real-time visualization of tissue surface biochemical features derived from optical signals.

Related Art

Optical spectroscopy and imaging techniques can provide useful information about structural, biochemical or functional properties of biological tissues. For example, such techniques can be used to diagnose human conditions, such as tumors or atherosclerotic plaques in the medical field, and to analyze the chemical or biochemical composition of organic matter in other fields. Multimodal imaging approaches have been implemented to enhance detection of complementary features in tissue. In this context, emphasis has recently been placed on the development of visualization methods enabling co-registration of information from distinct imaging modalities by means of real-time augmented reality. However, such methods have not been reported for point-scanning spectroscopic imaging techniques.

Although scanning techniques have shown potential to provide real-time feedback about the biochemical features of tissue at each measured location, their clinical implementation is still limited by the difficulty in registering dynamically the diagnostic information derived from optical parameters with the location where the optical measurement was taken. Scanning multispectral time-resolved fluorescence spectroscopy (ms-TRFS), for example, has demonstrated ability to rapidly characterize and diagnose diseased tissues based on their autofluorescence properties. Nevertheless, this technique, like other optical spectroscopy techniques (i.e., diffuse reflectance spectroscopy), lacks an efficient visualization method of the measured quantities making it prone to registration errors. Registering the diagnostic information is further complicated when wavelengths outside the human eye sensitivity are employed, such as the UV light for excitation of autofluorescence, or the intensity of the emitted light is below the sensitivity of conventional cameras. In such cases, the identification of the measured location is an additional challenge, because the operator cannot visually locate the interrogated area by tracking the excitation light on the tissue surface. A common approach to overcome these challenges is based on offline data analysis and registration based on structural landmarks or spatial sampling at predefined locations. However, this offline approach does not provide real-time feedback about biochemical features that can be extremely useful, for example, to guide a surgical procedure.

Hence, what is needed is an imaging technique that provides feedback about biochemical features of tissue without the above-described problems.

SUMMARY

The disclosed embodiments relate to a system that displays an image of the characteristics of the biological tissue. During operation, the system enables a user to illuminate a measurement location in an area of interest on the biological tissue by manipulating a point measurement probe, wherein the point measurement probe delivers both an excitation beam and an overlapping aiming beam that are visible to a camera. Next, the system obtains fluorescence information from a fluorescence signal emitted from the measurement location in response to the excitation beam. The system then captures an image of the area of interest using the camera and identifies a portion of the image that corresponds to the measurement location by identifying a location illuminated by the aiming beam. Finally, the system generates an overlay image by overlaying the fluorescence information onto the portion of the image that corresponds to the measurement location, and then displays the overlay image to a user.

In some embodiments, the system displays the overlay image in real-time, thereby enabling the user to manipulate the point measurement probe to illuminate a new measurement location, and to instantly receive fluorescence information for the new measurement location.

In some embodiments, while enabling the user to illuminate the measurement location, the system enables the user to move the point measurement probe to acquire fluorescence information from multiple measurement locations in the area of interest. Then, while overlaying the fluorescence information, the system simultaneously overlays fluorescence information from the multiple measurement locations onto a single image of the area of interest.

In some embodiments, while overlaying the fluorescence information, the system overlays a color representing the fluorescence information onto the portion of the image that corresponds to the measurement location.

In some embodiments, the fluorescence information includes fluorescence information gathered through different channels associated with different wavelengths of the fluorescence signal. In these embodiments, when the system receives a command from the user to switch display channels, the system displays fluorescence information obtained through a different channel in the overlay image.

In some embodiments, the fluorescence information includes information related to fluorescence spectroscopy.

In some embodiments, the fluorescence information includes information related to fluorescence decay.

In some embodiments, the area of interest comprises tissue that includes a tumor prior to a surgical procedure to remove the tumor.

In some embodiments, the area of interest comprises a region of tissue that previously included a tumor after a surgical procedure to remove the tumor.

In some embodiments, identifying the location illuminated by the aiming beam comprises identifying a location that is illuminated with light that matches a wavelength of the aiming beam.

In some embodiments, obtaining the fluorescence information from the fluorescence signal comprises: using a photomultiplier tube (PMT) to gather the fluorescence signal; and then processing the fluorescence signal to obtain the fluorescence information.

In some embodiments, the diagnostic information derived from the fluorescence signal emitted from the measurement location is projected onto the portion of the image that corresponds to the measurement location In some embodiments, the fluorescence information includes fluorescence information gathered through different channels associated with different wavelengths of the fluorescence signal. In these embodiments, when the system receives a command from the user to switch display channels, the system displays fluorescence information obtained by combining fluorescence information from different channels.

In some embodiments, the area of interest comprises a region of tissue with one or more specific anatomical/morphological features of interest (e.g., nerves, plaques, growth, etc).

In some embodiments, the area of interest comprises a biological specimen (e.g., pathological specimens).

In some embodiments, the area of interest can be in-vivo (e.g., in a patient or live animal) or ex-vivo (e.g., excised tissue specimens) or in-situ (e.g., developing tissue constructs).

In some embodiments, the area of interest may be associated with cardiology, oncology (e.g., tumor diagnosis, detection, and/or delineation), regenerative medicine (e.g., engineered tissue constructs, scaffolds, and/or grafts) and/or other biomaterials.

In some embodiments, the illuminated location is identified using the fluorescence emission signal.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 6A-6C illustrate an example where fluorescence data is painted onto a raw video stream in accordance with the disclosed embodiments.

DETAILED DESCRIPTION

Figure 1:
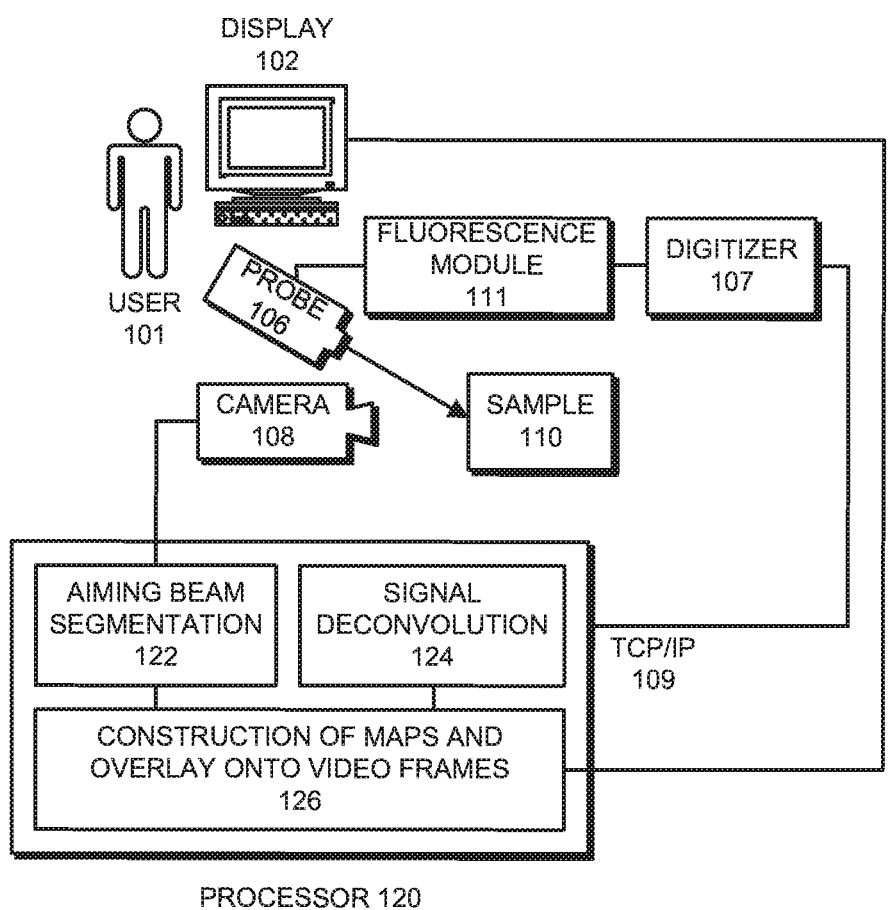
FIG. 1 illustrates a system for gathering fluorescence data in accordance with the disclosed embodiments.

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Overview

The disclosed embodiments make use of an optical beam (called an "aiming beam") to address the aforementioned challenges, thereby enabling a more effective and online application of the ms-TRFS technique in clinical settings. The concept of an aiming beam is presently used in ophthalmological applications for guidance during photocoagulation and safety measures for guidance of laser surgery procedures. The $CO_2$ laser typically used in such applications is invisible to the human eye. Nevertheless, the use of an aiming beam for online visualization of optical spectroscopy parameters carrying diagnostic information has as yet not been exploited.

The disclosed embodiments provide a novel framework that is compatible with intra-operative use of an aiming beam for online tracking and mapping of tissue biochemical properties. Specifically, we developed and validated a method that (i) extracts the aiming beam location from a video stream acquired by a camera, and (ii) overlays onto those images the fluorescence lifetime values as transparent pseudocolor masks. This provides dynamic visualization of the biochemical information of the measured points. Moreover, these pseudocolor masks can be dynamically updated during the scanning procedure, constructing fluorescence lifetime imaging (FLIm) maps of tissues. This technique is particularly well-suited to interventions already providing a live video stream of the operating field, such as some endoscopic or robotic-assisted interventions, and can easily be integrated to free-hand or motorized scanning applications with the addition of a camera to image the regions of interest. Moreover, the probe can be integrated with any surgical interventional tools (e.g., suctions probe and cautery tools and/or other tissue cutting tools)

Materials and Methods

The data flow of the disclosed method is depicted in FIG. 1. During operation of the system illustrated in FIG. 1, a user 101 (such as a surgeon) illuminates a sample of biological tissue 110 with a handheld probe 106 that emits both an excitation beam and an overlapping aiming beam that are visible to a camera 108. Probe 106 also gathers a fluorescence signal emitted from the measurement location in response to the excitation beam.

The system illustrated in FIG. 1 comprises two blocks 122 and 124 that operate in parallel; block 124 enables rapid fluorescence data analysis (including fluorescence transient signal deconvolution and average lifetime estimation), and block 122 enables extraction of the aiming beam from conventional white-light images obtained through camera 108. During system operation, fluorescence signals received through probe 106 are transmitted through a fluorescence module 111 (e.g., a (portion of a) time-domain ms-TRFS system) and a digitizer 107 to a processor 120 through TCP/IP sockets 109 and undergo a deconvolution process for the estimation of lifetime values in block 124. The locations of the measurements are identified by segmentation of the captured video frames. The results from blocks 122 and 124 are then combined by a third block 126, which constructs FLIm maps enabling the real-time output to a display 102 of the acquired video frames augmented with biochemical and/or functional information of the interrogated tissues by means of overlaid FLIm maps. Note that user 101 can selectively aim probe 106 to illuminate different locations in sample 110 to obtain this biochemical information through display 102 in real-time.

ms-TRFS System with Aiming Beam

Figure 2:
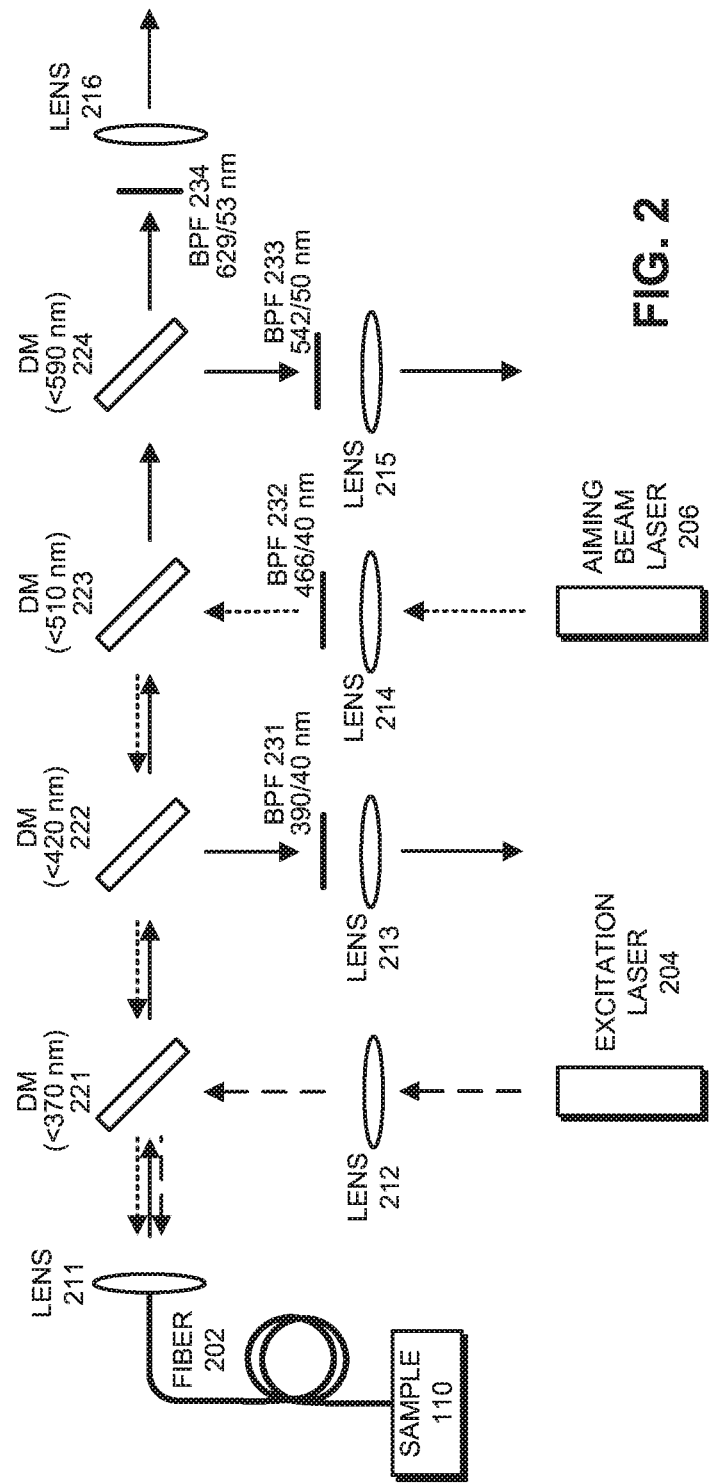
FIG. 2 illustrates a wavelength selection chamber in accordance with the disclosed embodiments.

A time-domain ms-TRFS system can be constructed as is illustrated in FIG. 2. As illustrated in FIG. 2, a micro Q-switched laser frequency tripled to 355 nm (Teem Photonics, France, 600 ps pulse width, 2 KHz repetition rate) can be used as an "excitation laser" 204 for fluorescence excitation. A single 400 µm core diameter silica fiber (Polymicro Technologies™, USA) can be used for both fluorescence excitation and collection. The proximal end of the fiber can be connected to a wavelength selection module (WSM) composed of a set of dichroic mirrors (DMs) 221-224 and band-pass filters (BPFs) 231-234 that can spectrally resolve the collected signal in four channels simultaneously: 390/40 nm (channel 1), 466/40 nm (aiming beam), 542/50 nm (channel 2), and 629/53 nm (channel 3). In the illustrated example, the second physical channel of the WSM is dedicated to the aiming beam delivery. A 450 nm beam from a continuous-wave diode laser (PL 450B, Osram, Germany), an "aiming beam laser" 206, can be coupled into this channel; thus, the aiming beam is delivered via the same optical path as the fluorescence excitation beam.

The incident power of the aiming beam on the sample is approximately 3 mW. The other three channels are connected to optical fibers of distinct lengths (acting as delay lines) coupled at their distal end into a single microchannel plate photomultiplier tube (MCP-PMT, R3809U-50, Hamamatsu, 45 ps FWHM). The fluorescence signals from the three channels, after being detected by the MCP-PMT and boosted by an RF amplifier (AM-1607-3000, 3 GHz bandwidth, Miteq, USA), are temporally resolved by the digitizer (PXIe-5185, National Instruments, 12.5 GS/s sampling rate) at 80 ps time intervals. An RF amplifier is AC coupled with a low cut-off frequency of 10 KHz. Therefore, the autofluorescence signal induced by the aiming beam (continuous-wave) can be filtered-out by the amplifier and is not present in the acquired data.

A CMOS camera 108 (FIG. 1) (UI144xSE-C, 1280×1024 pixels, 17 fps, IDS GmbH, Germany) can be used for imaging the area of interest during the experimental process. Camera 108's software development kit (SDK) can be used to set the acquisition parameters and capture the video frames. Note that the disclosed technique can be easily adapted to function with any conventional color camera.

Image analysis and ms-TRFS signal processing computations are implemented in C++ using the open source computer vision library OpenCV 3.0 (opencv.org). The personal computer on which these computations is performed is equipped with an Intel Core i7-3632QM CPU and 16 GB of RAM. ms-TRFS data acquisition and preprocessing can be implemented in the digitizer (Intel Celeron dual-core T3100 CPU, 3 GB RAM) with LabVIEW platform (National Instruments). The communication between the CPU and digitizer 107 can be implemented via a TCP/IP protocol, where digitizer 107 is serving as the host and processor 120 as the client.

Aiming Beam Imaging and Segmentation

Block 122 in FIG. 1 extracts the location of the aiming beam from each acquired frame. The wavelength of the aiming beam significantly affects the segmentation process. Shorter wavelengths of the visible spectrum present a limited penetration depth and consequently limited diffused reflectance. Such wavelengths would ensure that the projected aiming beam approximates the autofluorescence excitation source profile. In contrast, use of longer wavelengths for the aiming beam would lead to the segmentation of significantly larger areas than the actual areas of incidence of the excitation source. The aiming beam source (450 nm) has been chosen accordingly.

Block 122 comprises three processes. First, the acquired frames are transformed from the RGB to the HSV colorspace and thresholded for the hue values that correspond to the blue color [23] ($H_{threshold}$: 85-155/$H_{Blue}$=120 in OpenCV). To detect a wide range of blue intensities, value and saturation were both bounded between 50 and 255. These values might be subject to refinement when other blue or violet objects are present (e.g., surgical gloves). Application of this threshold to the fresh tissue depicted in FIG. 3A results in the binary image of FIG. 3B. (Note that FIGS. 3A-3D illustrate a section of an RGB frame displaying the aiming beam projected on a tissue sample shown in FIG. 3A, with the results of the color-based thresholding shown in FIG. 3B. The aiming beam is indicated by the blue arrow and the noise structure by the red ones. Morphological filtering is applied for image denoising in FIG. 3B, and the aiming beam is fitted to an ellipse to approximate its actual shape in FIG. 3D.)

Figure 3B:
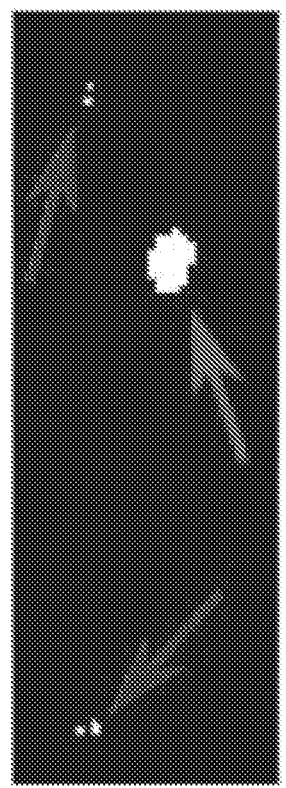
FIGS. 3A-3D illustrate the process of identifying a location illuminated by the aiming beam in accordance with the disclosed embodiments.
Figure 3D:
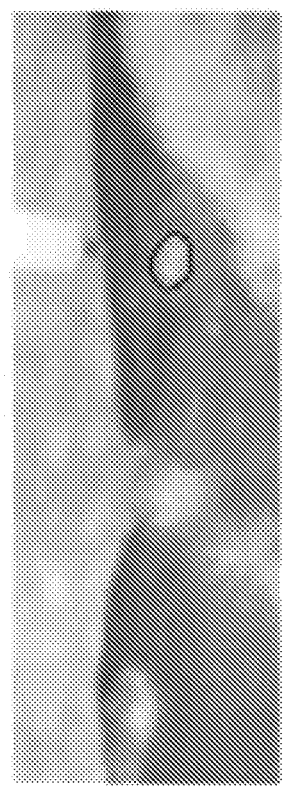
Figure 3A:
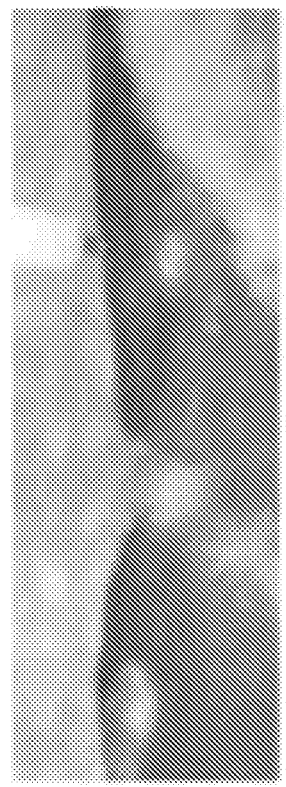
Figure 3C:
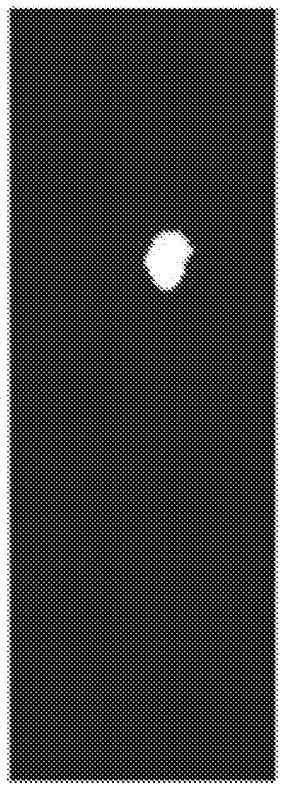

Second, the binary images undergo morphological filtering to remove any remaining noise. Specifically, a morphological dilation with a circular structured element with diameter equal to three pixels is initially applied to the image. Application of this filter ensures that the aiming beam will not appear broken in the binary image (i.e., a portion of the beam is invisible and appears as multiple small segments). This filter, however, also leads to enlarged noise artifacts. To account for this, denoising is applied through morphological erosion followed by a dilation. A circular structured element with diameter equal to seven pixels is used in both these filters. Thereafter, erosion with a three pixel diameter structured element is applied to restore the aiming beam to its original size. The result of this filtering sequence is shown in FIG. 3C.

Third, each element in the binary image (i.e., aiming beam plus any remaining noise artifacts) is fitted to an ellipse, to approximate the actual shape of the projected aiming beam. For each frame, the Euclidian distance between the center of the current ellipse and the one from the previous frame is estimated. The ellipse corresponding to the minimum distance is attributed to the aiming beam of FIG. 3D. Any frame where no aiming beam is detected is discarded, the method proceeds to the acquisition of the next frame, and for the new ellipse the Euclidian distance is estimated from the image center.

Fluorescence Signal Deconvolution

Ms-TRFS Signal Preprocessing—

Following the acquisition of each fluorescence transient signal, a background subtraction is applied (i.e., subtraction of a reference signal from the acquired fluorescence transient signals). The reference signal is acquired prior to the measurements and corresponds to the autofluorescence from the fiber. The embedded computer of the digitizer was used for signal preprocessing. TCP/IP sockets are then used to transfer the fluorescence signals to processor 120 in FIG. 1.

Ms-TRFS Signal Deconvolution (Block 124)—

Block 124 in FIG. 1 performs a deconvolution of the fluorescence decay signal. Constrained least-squares deconvolution with Laguerre expansion can be used to quantify the fluorescence decay characteristics. In time-domain, the fluorescence decay is usually expressed as follows:

$$y(k) = \sum_{i=0}^{k} I(k-i) \cdot h(k) + \varepsilon_k \quad (1)$$

where N is the number of the equally spaced sampling time points and $k=0, \ldots, N-1$. In equation (1), $y(k)$ is the kth measured decay, $I(k)$ is the instrument impulse response function (iIRF), and $h(k)$ is the fluorescence impulse response function (fIRF); $\varepsilon_k$ represents the additive measurement noise.

Based on the constrained least-squares method described, equation (1) can be approximated by the matrix formula:

$$\hat{h} = B \cdot \hat{c} \quad (2)$$

Where $B=[b_0, b_1, \ldots, b_{L-1}]$ are the L discrete time Laguerre basis functions. Moreover, $\hat{c}$ is the vector of the Laguerre coefficients and is approximated as:

$$\hat{c} = (V^{-1} \cdot V)^{-1} \cdot (V^T \cdot y - D^T \cdot \hat{\lambda}) \quad (3)$$

where V is the convolution of the iIRF with the Laguerre basis functions, and D is the third-order forward finite difference matrix and depends only on the length of the acquired signal vectors. Finally, $\hat{\lambda}$ is the Lagrangian multiplier, which is estimated by the non-negative least-squares problem:

$$\min_{\lambda} \|C \cdot (V^T \cdot y - D^T \cdot \lambda)\|^2, \text{ where } \lambda \geq 0 \quad (4)$$

with C being the Cholesky decomposition of the positive definite matrix $(V^T \cdot V)^{-1}$.

The matrices in equations (2) through (4) that are independent of the fluorescence signals can be estimated before any measurement is acquired. The deconvolution is then implemented via the following steps: (i) estimation of the Lagrangian multiplier from equation (4), (ii) estimation of the Laguerre coefficients from equation (3), and (iii) estimation of the fIRF from equation (2). The average lifetime values are approximated from the resultant fIRF. OpenCV functions are used for all the required computations, with the exception of the non-negative least-squares, which was a C++ version of the Lawson-Hanson method. This implementation of the deconvolution process reduces the computational time by approximately 35% (~2.4 ms per decay) when compared with an implementation based on MATLAB® (The Mathworks, Inc.) (~3.7 ms per decay). Further, this is achieved without any impact on the lifetime estimation accuracy, as expected.

Visualization of Lifetime Values Distribution

The third block 126 concerns the formation of the displayed frames, which comprises acquired white-light frames augmented with the FLIm maps. As shown in FIG. 1, block 126 has two inputs: (i) the location of the ellipse fitted to the aiming beam, and (ii) the corresponding lifetime values for the three WSM channels. This information is combined to create the FLIm maps and overlay them onto the acquired frames as pseudocolor transparent masks.

During scanning, however, consecutive ellipses can partially overlap. This can lead to pixelated lifetime visualization, especially when scanning the edges of fluorescence contrast regions. This is addressed by the per-pixel weighting of the lifetime corresponding to each ellipse:

$$\tau(u,v,k) = \left. \frac{\tau(u,v,k-1) \cdot [N(u,v)-1] + \tau(u,v,k)}{N(u,v)} \right|_{CHx} \quad (5)$$

where $\tau(u,v,k)$ is the lifetime for channel CHx, and $x=1, 2, 3$, at $(u,v)$ pixel and $k^{th}$ frame. $N(u,v)$ is the accumulated index of how many times pixel $(u,v)$ was visited during the scan. There is a distinct index $N(u,v)$ per channel of the WSM. Combining equation (5) with the ellipse fitted to the aiming beam, three masks are constructed with the weighted lifetime values (one mask for each WSM channel). These masks are dynamically updated as the scan is progressing.

The FLIm maps (pseudocolor versions of lifetime masks) are also constructed, where the color of each pixel is determined by user-defined lower- and upper-bounds of lifetime values. These bounds can be updated online during the scan, an action that instantly updates the entirety of the FLIm maps. The user can also select which one of the three channels will be overlaid onto the acquired frames. The overlay is implemented through a weighted sum:

$$I_{out}(M \neq 0) = a \cdot I_{in}(M \neq 0) + (1-a) \cdot M(M \neq 0) \quad (6)$$

where $I_{in}$ is the acquired frame, $I_{out}$ is the displayed frame, M is the FLIm map of the channel CHx and $a=[0,1]$ is the weight factor determining the transparency of the overlaid map. Similarly to equation (5), the weighted sum is applied only to the pixels visited during the scanning process.

The two images, $I_{in}$ and $I_{out}$, are finally combined into one with $(2 \cdot N) \times M$ pixels, with the columns and the rows of the acquired frame. This image contains both the white-light version of the scene ($I_{in}$) and the same white-light version augmented with the selected FLIm map ($I_{out}$). For the image to fit within a high-definition (HD) monitor, the frames after acquisition are scaled accordingly if the dimension $2 \cdot N$ exceeds the width of HD resolution (1920 pixels).

Scaling of the Ellipse Fitted to the Aiming Beam

The distinct tissue optical properties, at the aiming beam (450 nm) and the excitation light (355 nm) wavelengths, result in differences between the area of the imaged aiming beam and the area where fluorescence is measured. The area over which fluorescence signals are measured is approximately equal to the size of the fiber core, when the probe-to-target distances are smaller than 3 mm. As expected, though, in FIG. 3D the aiming beam covers a much larger area even though the probe-to-target distance is approximately 2 mm.

Figure 4A:
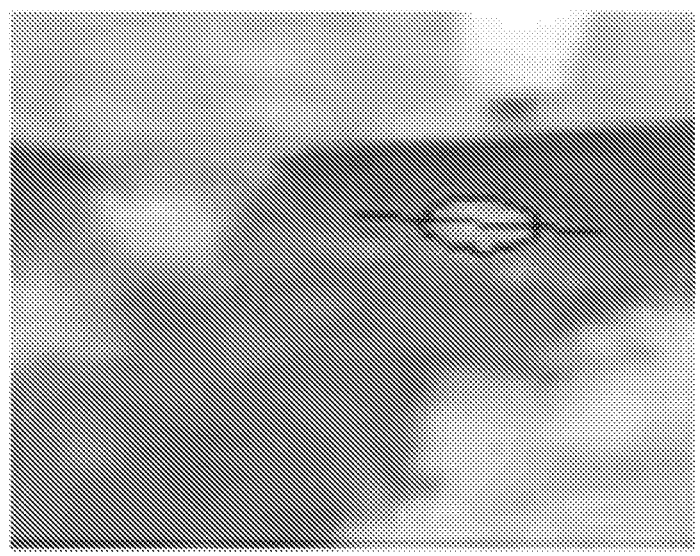
FIGS. 4A-4B illustrate how the size of the excitation beam is determined by assuming a Gaussian distribution in accordance with the disclosed embodiments.
Figure 4B:
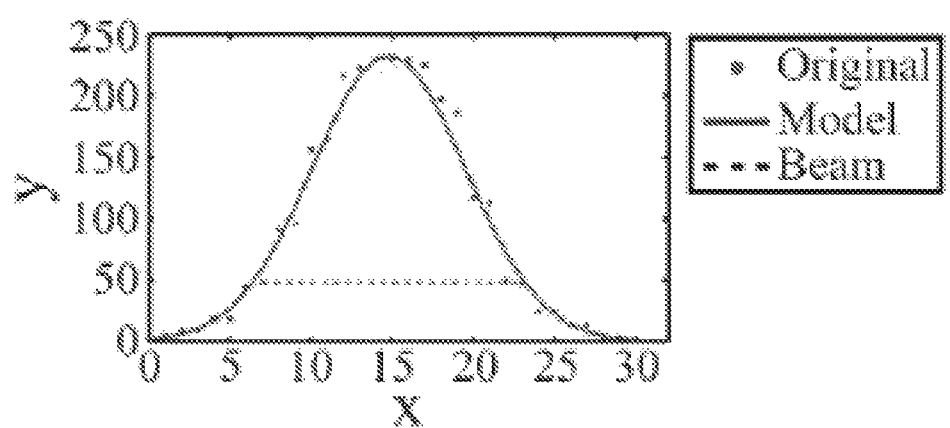

To address this mismatch between the incident and imaged beam size, we derived the size of the excitation beam by assuming a Gaussian distribution of the aiming beam's intensity profile. Specifically, this distribution was centered to the center of the ellipse fitted to the aiming beam and its maximum spread was set equal to twice the length of the ellipse's major axis, as is illustrated in FIGS. 4A-4B. The parameters of the Gaussian distribution were approximated by solving the linear system:

$$\begin{bmatrix} y_0 \\ \vdots \\ y_{N-1} \end{bmatrix} = \begin{bmatrix} x_0^2 & x_0 & 1 \\ \vdots & \vdots & \vdots \\ x_{N-1}^2 & x_{N-1} & 1 \end{bmatrix} \cdot \begin{bmatrix} P \\ Q \\ R \end{bmatrix} \quad (7)$$

for the white-light frame pixels corresponding to the distribution's maximum spread. In equation (7), N is the number of pixels, $y_i$ is the natural logarithm of the $i^{th}$ pixel's blue channel intensity, after subtracting the baseline (i.e., minimum value), $x_i$=i are the one-dimensional pixel coordinates (i=0, . . . , N-1). Assuming a Gaussian function:

$$y = A \cdot \exp[-(x-\mu)^2/(2 \cdot \sigma^2)] \quad (8)$$

the mean $\mu = -Q/(2 \cdot P)$, variance $\sigma^2 = -1/(2 \cdot P)$ and weight $A = \exp[R - Q^2/(4 \cdot P)]$ can be approximated by solving equation (7). One example of this fitting is shown in FIG. 4B. (Note that FIGS. 4A and 4B illustrate how the Gaussian distribution's maximum spread is equal to twice the length of the ellipse's major axis as shown in FIG. 4A and the Gaussian fit of the blue channel's intensity values of the corresponding pixels as shown in FIG. 4B. The dashed line is the major axis of the ellipse fitted to the segmented aiming beam.)

These parameters are then used to dynamically define the size of the ellipse fitted to the aiming beam. Specifically, three widths are used: (i) the full width half maximum (FWHM), (ii) the full width at 75% of the maximum (FW0.75M), and (iii) the full width at 90% of the maximum (FW0.9M) of the Gaussian fit. The ellipse was then scaled by considering the ratio among these three widths and its major axis length. The first width (FWHM) is approximately equal to the major axis of the ellipse fitted to the detected aiming beam (FIG. 4A). The FW0.9M of the Gaussian fit is a typical threshold to extract the peak values of a Gaussian distribution, while the FW0.75M is an intermediate width. These widths can be quantified through the variance of the Gaussian distribution:

$$FW0.XM = 2 \cdot \sigma \cdot \sqrt{-2 \cdot \ln(0.X)} \quad (9)$$

where 0.X is the percentage of the Gaussian distribution's maximum value for thresholding.

Figure 5B:
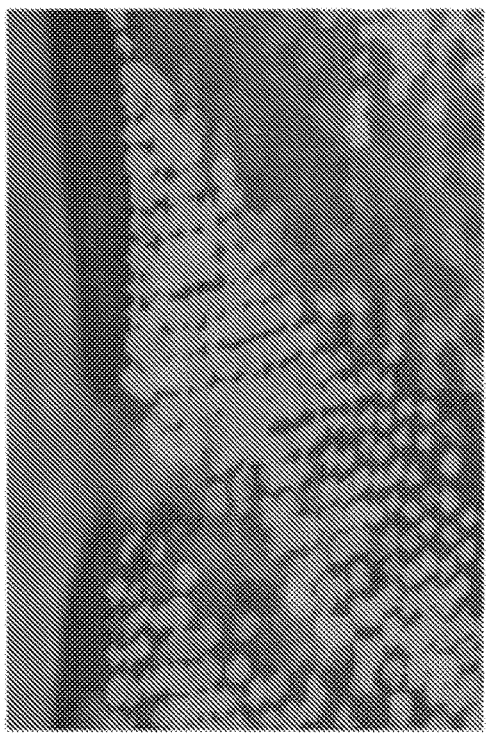
FIGS. 5A-5D illustrate an example where lamb tissue is augmented with FLIm maps in accordance with the disclosed embodiments.
Figure 5D:
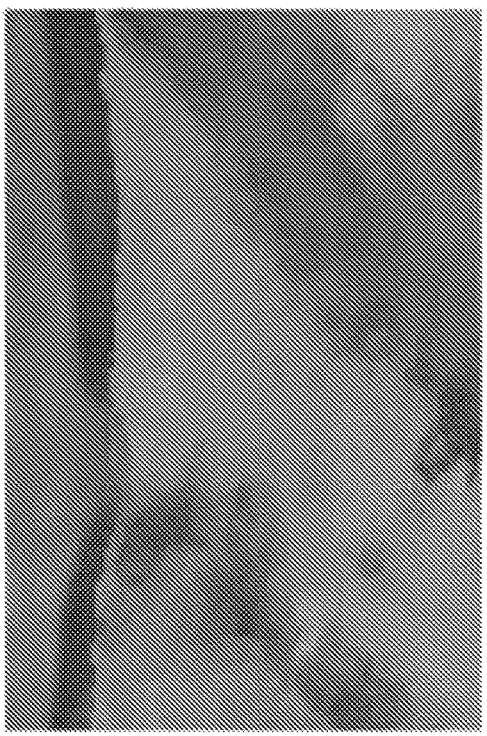
Figure 5A:
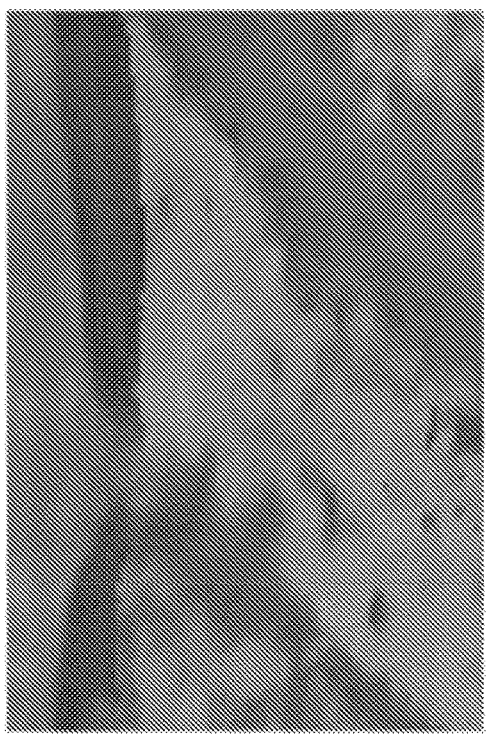
Figure 5C:
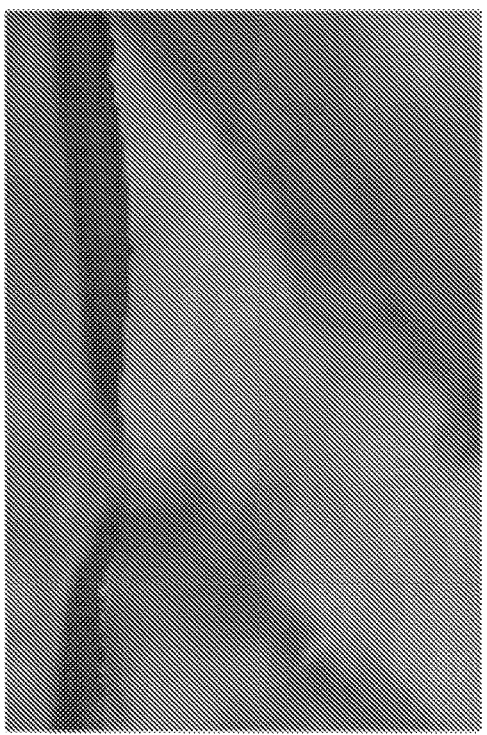

Working with a constant scale of the detected aiming beam can, however, lead to either sparse fluorescence lifetime information overlaid onto the white-light frames or to smooth/blurred FLIm maps due to equation (5). This problem is demonstrated in FIGS. 5A-5D. For example, FIG. 5A shows a white-light image from fresh lamb tissue augmented with the FLIm map from the first channel of the WSM and for a v=2 mm/s scanning speed. In this case the ellipse fitted to the aiming beam was scaled to the FW0.9M of the Gaussian distribution resulting from equation (8). The derived FLIm map is dense and the edges between the lifetime contrast sources are sharp. On the other hand, increasing the scanning speed (v=20 mm/s in FIG. 5B), while the frame rate of the method remains constant, results in a sparse FLIm map (FIG. 5B). This can be addressed by using larger ellipses (see FIGS. 5C and 5D). The improved coverage for higher scanning speeds is obtained at the cost of a reduced spatial resolution of the constructed FLIm maps. (FIGS. 5A-5D illustrate white-light images from fresh lamb tissue, augmented with FLIm maps from the first channel of the WSM for the FW0.9M (see FIG. 5A and FIG. 5B) and FWHM (see FIG. 5C and FIG. 5D). Scales of the ellipse are fitted to the aiming beam and for v=2 mm/s (see FIG. 5A and FIG. 5C) and v=20 mm/s, (see FIG. 5B and FIG. 5D) scanning speeds. Lifetime values are bounded between 2 ns (blue) and 7 ns (red). Images were cropped and enlarged for optimized visualization.)

Thus, there is a compromise among speed, algorithm frame rate, and spatial resolution. To address this compromise, the ellipse fitted to the aiming beam is automatically scaled based on the following three rules:

$$E = \quad (10)$$
$$\begin{cases} E_{FW0.9M} + E_{FW0.75M}(E_{FW0.9M} = 0), & \text{if } d \le D_{FW0.9M} \\ E_{FW0.75M} + E_{FWHM}(E_{FW0.75M} = 0), & \text{if } D_{FW0.9M} < d \le D_{FW0.75M} \\ E_{FWHM}, & \text{else} \end{cases}$$

where E are the FLIm maps and are constructed for all scales, d is the Euclidian distance between the centers of ellipses from two sequential frames, and D is the major axis length of the current ellipse. In case no aiming beam is detected for a certain frame, then this frame is discarded and for the following one distance d is estimated from the image center.

Multi-Threading Architecture

To increase the time efficiency of the current method, we can take advantage of the multi-threading capabilities of modern CPUs that allow for the parallelization of most processes within blocks 122 and 124 in FIG. 1.

Two points can be considered when designing the multi-threading algorithm. The first is the parallel acquisition of the image frame and the ms-TRFS data, which ensures that both modalities are synced. The second is the parallelization of processes that can slow the overall speed under sequential implementation. The speed can be determined by the slowest process and not by the accumulated time of all processes. This can be achieved by introducing a two-frame latency.

Specifically, for the first iteration one thread is dedicated to the first frame acquisition and a second thread to the corresponding ms-TRFS signal acquisition and deconvolution. For the second iteration, the second frame is acquired at one thread, the corresponding ms-TRFS signal is acquired and deconvolved at a second frame, and the previous frame is segmented at a third frame. These two iterations correspond to the two-frame latency. Starting with the third iteration, the multi-threading architecture includes the following threads: (i) one for acquisition of the current frame, (ii) one for acquisition and deconvolution of the corresponding ms-TRFS signal, (iii) one for segmentation of the previous frame, (iv) three for construction of the FLIm maps (i.e., one per WSM channel) of the data acquired two iterations before the current iteration, and (v) one for data saving (i.e., video sequence, lifetime values). After all thread workers are completed, the weighted sum between the FLIm maps and the corresponding white-light frames is formed based on equation (6).

Example of Imaging Fresh Tissue Samples

Motorized and free-hand scanning measurements were acquired from fresh porcine and lamb tissue samples for various scanning speeds and areas. These measurements were made in order to demonstrate the functionality of the current method (i.e., motorized raster scanning, free-hand scanning), as well as its capability to enable visualization of localized distinct sources of lifetime contrast in biological tissues (i.e., fat, muscle, bone).

The motorized raster scanning measurements were made on porcine tissue samples, with ellipses corresponding to the FWHM, FW0.75M, and FW0.9M of the Gaussian fit described above, as well as automated scaling of the ellipse fitted to the aiming beam. The imaged area for all measurements was equal to 20 mm×25 mm and the scanning speeds ranged from v=2 mm/s up to v=30 mm/s with a raster pitch equal to dy=0.5 mm. Through these measurements, the impact of the ellipse's automated scaling on the construction of the FLIm maps was demonstrated and compared to the fixed scaling.

The robustness of the method to provide the same FLIm maps regardless of the scanning mode (motorized raster or free-hand scanning) was demonstrated with measurements on the fresh lamb tissue samples. The motorized raster scanning measurements were acquired from a 25 mm×25 mm region with speed v=6 mm/s and vertical step dy=0.5 mm.

Two representative screenshots from motorized and hand-held scanning as seen in the GUI display window are shown in FIGS. 6A and 6B for the 390/40 nm (channel 1) and 540/50 nm (channel 2) bands of the WSM. (Note that the raw video stream is displayed for reference and guidance in FIG. 6A.) Both screenshots were captured during the same scanning session on fresh lamb tissue. The displayed channel of the WSM can be changed online during the scanning. The pseudocolor range of the FLIm maps can be also updated online during the scanning procedure.

As seen in FIG. 6A, additional information about the scanning process, such as the processing and camera frame rates (top left of the display window), the processed and skipped frames (bottom right), and the channel currently displayed (top left of the augmented image), is further displayed in the GUI. Finally, a different transparency level is applied between FIG. 6A and FIG. 6B, and can also be changed online during the scanning measurements.

Besides motorized raster scanning applications, the proposed method was also tested with hand-held scanning. For example, the overlay at 542/50 nm of handheld scanning at the same tissue is shown in FIG. 6C, which depicts one representative screenshot from hand-held scanning measurements on the fresh lamb tissue sample. As mentioned above, the presence of the purple glove in the imaging scene required refinement of the saturation parameter of the HSV thresholding. In this case, a saturation lower limit equal to 150 was adequate for completely removing the glove area from the binary image.

Summary of System Operation

Figure 7:
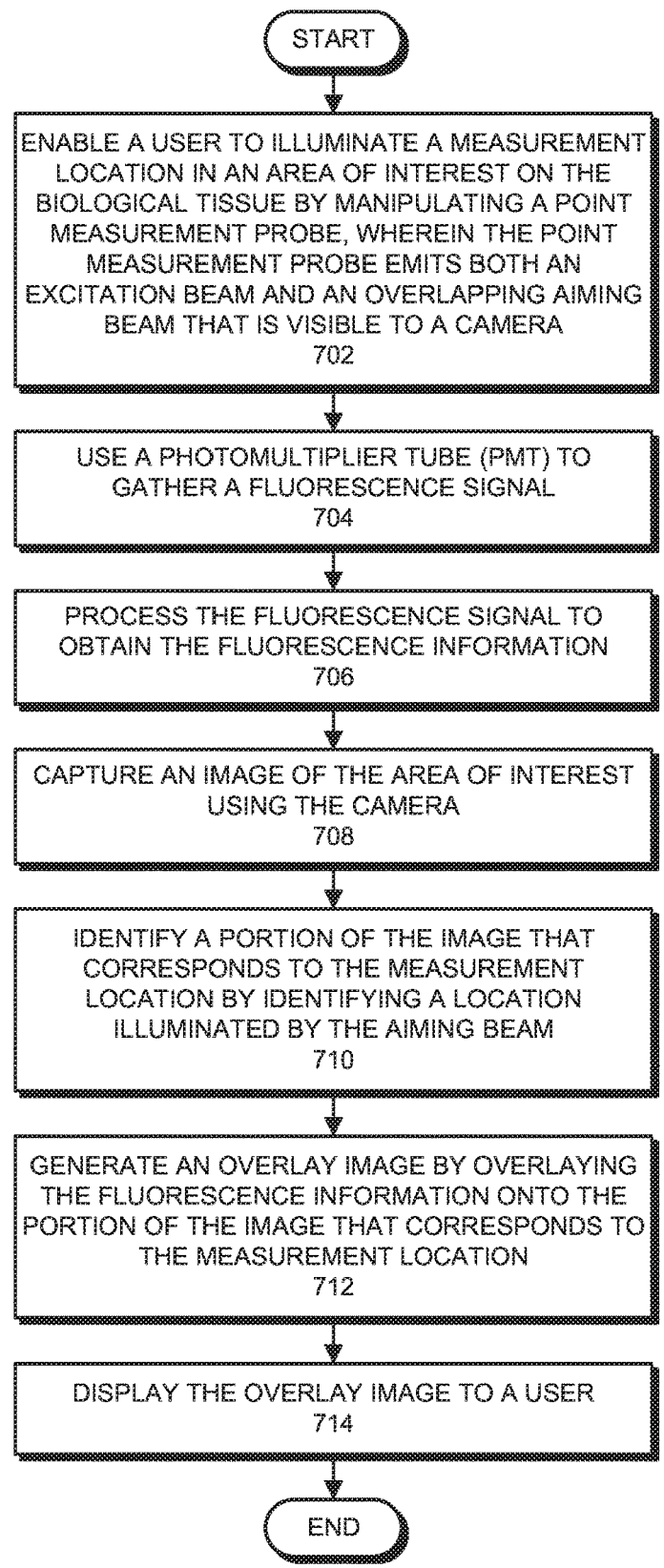
FIG. 7 presents a flow chart illustrating how an overlay image is generated and displayed in accordance with the disclosed embodiments.

FIG. 7 presents a flow chart illustrating how the system generates and displays an overlay image in accordance with the disclosed embodiments. During operation, the system enables a user to illuminate a measurement location in an area of interest on the biological tissue by manipulating a point measurement probe, wherein the point measurement probe emits both an excitation beam and an overlapping aiming beam that is visible to a camera (step 702). Next, the system uses a photomultiplier tune (PMT) to gather a fluorescence signal (step 704), and processes the fluorescence signal to obtain the fluorescence information (step 706). The system then captures an image of the area of interest using the camera (step 708), and identifies a portion of the image that corresponds to the measurement location by identifying a location illuminated by the aiming beam (step 710). Finally, the system generates an overlay image by overlaying the fluorescence information onto the portion of the image that corresponds to the measurement location (step 712), and displays the overlay image to a user (step 714).

Figure 8:
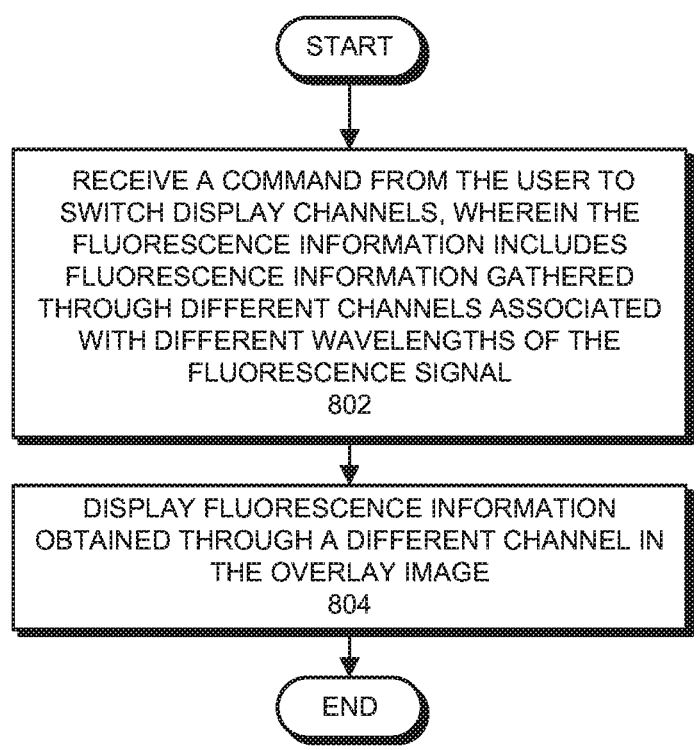
FIG. 8 presents a flow chart illustrating how display channels are switched in accordance with the disclosed embodiments.

FIG. 8 presents a flow chart illustrating how display channels can be switched in accordance with the disclosed embodiments. During this process, the system receives a command from the user to switch display channels, wherein the fluorescence information includes fluorescence information gathered through different channels associated with different wavelengths of the fluorescence signal (step 802). In response to this command, the system displays fluorescence information obtained through a different channel in the overlay image (step 804).

Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the principles and features disclosed herein.

The foregoing descriptions of embodiments have been presented for purposes of illustration and description only. They are not intended to be exhaustive or to limit the present description to the forms disclosed. Accordingly, many modifications and variations will be apparent to practitioners skilled in the art. Additionally, the above disclosure is not intended to limit the present description. The scope of the present description is defined by the appended claims.

What is claimed is:

1. A method for displaying an image of organic material, the method comprising:
   enabling a user to illuminate a point measurement location in an area of interest on the organic material by manipulating a fiber-optic point measurement probe, wherein the point measurement probe delivers both a fluorescent excitation beam and an overlapping aiming beam that is visible to a camera;
   wherein the point measurement probe also gathers a point measurement comprising fluorescence information from a fluorescence signal emitted from the point measurement location in response to the fluorescent excitation beam;
   wherein the point measurement location from which the fluorescence information is gathered has a size that is equivalent in magnitude to a size of a fiber optic core in the point measurement probe through which the fluorescent excitation beam is delivered;
   filtering out an auto-fluorescence signal induced by the aiming beam from the fluorescence information for the point measurement by,
      using dichroic mirrors and band pass filters to spectrally resolve the fluorescence information into a set of channels, including a channel for the aiming beam, and
      using an amplifier to boost fluorescence signals from the set of channels, excluding the channel for the aiming beam, to produce filtered fluorescence information for the point measurement;
   capturing an image of the area of interest using the camera;
   identifying a portion of the image that corresponds to the point measurement location by identifying a location on the image, which is illuminated by the aiming beam;

generating a fluorescent overlay image by overlaying the fluorescence information onto the portion of the image that corresponds to the point measurement location; and displaying the fluorescent overlay image to a user.

2. The method of claim 1, wherein the method is performed in real-time, thereby enabling the user to manipulate the point measurement probe to illuminate a new point measurement location, and to instantly receive fluorescence information for the new point measurement location.

3. The method of claim 1,
wherein enabling the user to illuminate the point measurement location comprises enabling the user to move the point measurement probe to acquire fluorescence information from multiple point measurement locations in the area of interest; and
wherein overlaying the fluorescence information comprises simultaneously overlaying fluorescence information from the multiple point measurement locations onto a single fluorescent image of the area of interest.

4. The method of claim 1, wherein overlaying the fluorescence information involves overlaying a color representing the fluorescence information onto the portion of the image that corresponds to the point measurement location.

5. The method of claim 1,
wherein the fluorescence information includes fluorescence information gathered through different channels associated with different wavelengths of the fluorescence signal; and
wherein in response to receiving a command from the user to switch display channels, displaying fluorescence information obtained through a different channel in the fluorescent overlay image.

6. The method of claim 1, wherein the fluorescence information includes information related to fluorescence spectroscopy.

7. The method of claim 1, wherein the fluorescence information includes information related to fluorescence temporal characteristics.

8. The method of claim 1, wherein the area of interest comprises tissue that includes a tumor prior to a surgical procedure to remove the tumor.

9. The method of claim 1, wherein the area of interest comprises a region of tissue that previously included a tumor after a surgical procedure to remove the tumor.

10. The method of claim 1, wherein identifying the location illuminated by the aiming beam comprises identifying a location that is illuminated with light that matches a wavelength of the aiming beam.

11. The method of claim 1, wherein obtaining the fluorescence information from the fluorescence signal comprises:
using an optical detector to gather the fluorescence signal; and
processing the fluorescence signal to obtain the fluorescence information.

12. A system that displays an image of organic material, comprising:
a fiber-optic point measurement probe that enables a user to illuminate a point measurement location in an area of interest on the organic material, wherein the point measurement probe delivers both a fluorescent excitation beam and an overlapping aiming beam that is visible to a camera;
wherein the point measurement probe also gathers a point measurement comprising a fluorescence signal emitted from the point measurement location in response to the fluorescent excitation beam;
wherein the point measurement location from which the fluorescence signal is emitted is has a size that is equivalent in magnitude to a size of a fiber optic core in the point measurement probe through which the fluorescent excitation beam is delivered;
a fluorescence-processing mechanism that processes the fluorescence signal to obtain fluorescence information of the point measurement location;
wherein the fluorescence-processing mechanism filters out an auto-fluorescence signal induced by the aiming beam from the fluorescence information for the point measurement by,
using dichroic mirrors and band pass filters to spectrally resolve the fluorescence information into a set of channels, including a channel for the aiming beam, and
using an amplifier to boost fluorescence signals from the set of channels, excluding the channel for the aiming beam, to produce filtered fluorescence information for the point measurement;
the camera that captures an image of the area of interest;
an overlay-processing mechanism that,
identifies a portion of the image corresponding to the point measurement location by identifying a location on the image, which is illuminated by the aiming beam, and
generates a fluorescent overlay image by overlaying the fluorescence information onto the portion of the image that corresponds to the point measurement location; and
a display that displays the fluorescent overlay image to a user.

13. The system of claim 12, wherein the system displays the fluorescent overlay image in real-time, thereby enabling the user to manipulate the point measurement probe to illuminate a new point measurement location, and to instantly receive fluorescence information for the new point measurement location.

14. The system of claim 12, wherein when the user moves the point measurement probe to acquire fluorescence information from multiple point measurement locations in the area of interest, the overlay-processing mechanism simultaneously overlays fluorescence information from the multiple point measurement locations onto a single fluorescent image of the area of interest.

15. The system of claim 12, wherein while overlaying the fluorescence information, the overlay-processing mechanism overlays a color representing the fluorescence information onto the portion of the image that corresponds to the point measurement location.

16. The system of claim 12,
wherein the fluorescence information includes fluorescence information gathered through different channels associated with different wavelengths of the fluorescence signal; and
wherein in response to receiving a command from the user to switch display channels, the system displays fluorescence information obtained through a different channel in the fluorescent overlay image.

17. The system of claim 12, wherein the fluorescence information includes information related to fluorescence spectroscopy.

18. The system of claim 12, wherein the fluorescence information includes information related to fluorescence temporal characteristics.

19. The system of claim 12, wherein the area of interest comprises tissue that includes a tumor prior to a surgical procedure to remove the tumor.

20. The system of claim 12, wherein the area of interest comprises a region of tissue that previously included a tumor after a surgical procedure to remove the tumor.

21. The system of claim 12, wherein while identifying the location illuminated by the aiming beam, the overlay-processing mechanism identifies a location that is illuminated with light that matches a wavelength of the aiming beam.

22. The system of claim 12, wherein the fluorescence sensor comprises a photomultiplier tube (PMT).

23. A non-transitory computer-readable storage medium storing instructions that when executed by a computer cause the computer to perform a method for displaying an image of organic material, the method comprising:

enabling a user to illuminate a point measurement location in an area of interest on the organic material by manipulating a fiber-optic point measurement probe, wherein the point measurement probe delivers both a fluorescent excitation beam and an overlapping aiming beam that is visible to a camera;

wherein the point measurement probe also gathers a point measurement comprising fluorescence information from a fluorescence signal emitted from the point measurement location in response to the fluorescent excitation beam;

wherein the point measurement location from which the fluorescence information is gathered has a size that is equivalent in magnitude to a size of a fiber optic core in the point measurement probe through which the fluorescent excitation beam is delivered;

filtering out an auto-fluorescence signal induced by the aiming beam from the fluorescence information for the point measurement by,
using dichroic mirrors and band pass filters to spectrally resolve the fluorescence information into a set of channels, including a channel for the aiming beam, and
using an amplifier to boost fluorescence signals from the set of channels, excluding the channel for the aiming beam, to produce filtered fluorescence information for the point measurement;

capturing an image of the area of interest using the camera;

identifying a portion of the image that corresponds to the point measurement location by identifying a location on the image, which is illuminated by the aiming beam;

generating a fluorescent overlay image by overlaying the fluorescence information onto the portion of the image that corresponds to the point measurement location; and displaying the fluorescent overlay image to a user.

24. The non-transitory computer-readable storage medium of claim 23, wherein diagnostic information derived from the fluorescence signal emitted from the point measurement location is projected onto the portion of the image that corresponds to the point measurement location.

25. The non-transitory computer-readable storage medium of claim 23, wherein the fluorescence information includes fluorescence information gathered through different channels associated with different wavelengths of the fluorescence signal; and wherein in response to receiving a command from the user to switch display channels, displaying fluorescence information obtained by combining fluorescence information from different channels.

26. A method for displaying an image of organic material, the method comprising:

enabling a user to illuminate a point measurement location in an area of interest on the organic material by manipulating a fiber-optic point measurement probe, wherein the point measurement probe delivers both an excitation beam and an overlapping aiming beam that is visible to a camera;

wherein the point measurement probe also gathers a point measurement comprising optical information from an optical signal emitted from the point measurement location in response to the excitation beam;

wherein the point measurement location from which the optical information is gathered has a size that is equivalent in magnitude to a size of a fiber optic core in the point measurement probe through which the excitation beam is delivered;

filtering out an auto-fluorescence signal induced by the aiming beam from the optical information for the point measurement by,
using dichroic mirrors and band pass filters to spectrally resolve the fluorescence information into a set of channels, including a channel for the aiming beam, and
using an amplifier to boost fluorescence signals from the set of channels, excluding the channel for the aiming beam, to produce filtered fluorescence information for the point measurement;

capturing an image of the area of interest using the camera;

identifying a portion of the image that corresponds to the point measurement location by identifying a location on the image, which is illuminated by the aiming beam;

generating an overlay image by overlaying the optical information onto the portion of the image that corresponds to the point measurement location; and displaying the overlay image to a user.

27. A method for maintaining tissue light exposure within safety limits during an acquisition of optical measurements using a fiber-optic point measurement probe, which delivers a fluorescent excitation beam and an aiming beam on tissue, and also gathers a point measurement comprising fluorescence information from a fluorescence signal emitted from the point measurement location in response to the fluorescent excitation beam, and wherein the point measurement location from which the fluorescence information is gathered has a size that is equivalent in magnitude to a size of a fiber optic core in the point measurement probe through which the fluorescent excitation beam is delivered, wherein an auto-fluorescence signal induced by the aiming beam is filtered out from the fluorescence information for the point measurement by, using dichroic mirrors and band pass filters to spectrally resolve the fluorescence information into a set of channels, including a channel for the aiming beam, and using an amplifier to boost fluorescence signals from the set of channels, excluding the channel for the aiming beam, to produce filtered fluorescence information for the point measurement, wherein the method comprises:

capturing an image of the area of interest using the camera;

identifying a portion of the image that corresponds to the location where light is being delivered by identifying a location on the image, which is illuminated by the aiming beam;

determining a maximum authorized light exposure in this location;

generating a fluorescent overlay image by applying an estimated fluorescent light exposure with respect to the maximum authorized light exposure onto the portion of the image that corresponds to the point measurement location; and displaying the fluorescent overlay image to a user.

28. The method of claim 27, wherein enabling the user to illuminate the point measurement location comprises enabling the user to move the point measurement probe to illuminate multiple point measurement locations in the area of interest; and wherein overlaying the delivered light information comprises simultaneously overlaying delivered light information from the multiple point measurement locations onto a single fluorescent image of the area of interest showing the current exposure with respect to the maximum authorized light exposure.

* * * * *